(12) United States Patent
Martinez Botella et al.

(10) Patent No.: US 11,407,782 B2
(45) Date of Patent: *Aug. 9, 2022

(54) OXYSTEROLS AND METHODS OF USE THEREOF

(71) Applicant: Sage Therapeutics, Inc., Cambridge, MA (US)

(72) Inventors: Gabriel Martinez Botella, Wayland, MA (US); Boyd L. Harrison, Princeton Junction, NJ (US); Albert Jean Robichaud, Boston, MA (US); Francesco G. Salituro, Marlborough, MA (US)

(73) Assignee: SAGE THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/930,047

(22) Filed: Jul. 15, 2020

(65) Prior Publication Data
US 2021/0171567 A1    Jun. 10, 2021

Related U.S. Application Data

(63) Continuation of application No. 16/099,122, filed as application No. PCT/US2017/031374 on May 5, 2017, now Pat. No. 10,752,653.

(60) Provisional application No. 62/332,959, filed on May 6, 2016.

(51) Int. Cl.
*C07J 9/00* (2006.01)

(52) U.S. Cl.
CPC ............... *C07J 9/00* (2013.01); *C07J 9/005* (2013.01); *C07B 2200/05* (2013.01)

(58) Field of Classification Search
CPC ................... C07J 9/005; C07B 2200/05
See application file for complete search history.

(56) References Cited

U.S. PATENT DOCUMENTS

| | | | |
|---|---|---|---|
| 2,594,323 A | 4/1952 | Levin et al. | |
| 2,673,206 A | 3/1954 | Ryer | |
| 3,079,385 A | 2/1963 | Bertin et al. | |
| 3,206,459 A | 9/1965 | Cross | |
| 4,071,625 A | 1/1978 | Grunwell et al. | |
| 4,174,345 A | 11/1979 | Kaiser | |
| 4,183,852 A | 1/1980 | Kaiser | |
| 4,868,165 A | 9/1989 | Ikekawa | |
| 5,232,917 A | 8/1993 | Bolger et al. | |
| 5,376,645 A | 12/1994 | Stella et al. | |
| 5,512,570 A | 4/1996 | Dorn et al. | |
| 5,595,996 A | 1/1997 | Graham et al. | |
| 5,888,996 A | 3/1999 | Farb | |
| 5,925,630 A | 7/1999 | Upasani et al. | |
| 6,407,086 B2 | 6/2002 | Faarup et al. | |
| 6,645,953 B2 | 11/2003 | Gronvald et al. | |
| 6,884,796 B2 | 4/2005 | Faarup et al. | |
| 6,933,312 B2 | 8/2005 | Price et al. | |
| 8,034,798 B2 | 10/2011 | Baulieu et al. | |
| 8,247,436 B2 | 8/2012 | Baettig et al. | |
| 8,604,011 B2 | 12/2013 | Mellon | |
| 8,673,843 B2 | 3/2014 | Moskal et al. | |
| 8,829,213 B2 | 9/2014 | Peng et al. | |
| 10,201,550 B2 | 2/2019 | Salituro et al. | |
| 10,227,375 B2 | 3/2019 | Botella et al. | |
| 10,259,840 B2 | 4/2019 | Harrison et al. | |
| 10,696,712 B2 | 6/2020 | Salituro et al. | |
| 10,723,758 B2 | 7/2020 | Harrison et al. | |
| 10,759,828 B2 | 9/2020 | Upasani et al. | |
| 11,104,701 B2 | 8/2021 | Martinez Botella et al. | |

(Continued)

FOREIGN PATENT DOCUMENTS

| | | |
|---|---|---|
| AU | 728843 | 1/2001 |
| CN | 1257077 | 6/2000 |

(Continued)

OTHER PUBLICATIONS

Nickmann-Pick overview [online] retrieved from the internet on Jul. 17, 2021 ((<URL:http://www.mayoclinic.org/diseases-conditions/niemann-pick/symptoms-causes/syc-2035>).*

Nickmann-Pick diagnosis-treatment [online] retrieved from the internet on Jul. 17, 2021 ((<URL: http://www.mayoclinic.org/diseases-conditions/niemann-pick/diagnosis-treatment/drc-2)).*

U.S. Appl. No. 15/742,424, filed Jan. 5, 2018, Francesco G. Salituro et al., Pending.

(Continued)

*Primary Examiner* — Shawquia Jackson
(74) *Attorney, Agent, or Firm* — Haley Guiliano LLP; Karen Mangasarian

(57) ABSTRACT

Compounds are provided according to Formula (III):

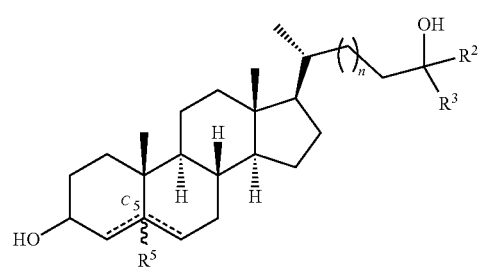

(III)

and pharmaceutically acceptable salts thereof, and pharmaceutical compositions thereof; wherein $R^2$, $R^3$, $R^5$, and n are as defined herein, and at least one hydrogen is replaced with a deuterium. Compounds of the present invention are contemplated useful for the prevention and treatment of a variety of conditions.

22 Claims, No Drawings

(56) References Cited

U.S. PATENT DOCUMENTS

| | | | |
|---|---|---|---|
| 11,111,266 B2 | 9/2021 | Salituro et al. |
| 11,149,054 B2 | 10/2021 | Salituro et al. |
| 2004/0048838 A1 | 3/2004 | Gronvald et al. |
| 2005/0101573 A1 | 5/2005 | Faarup et al. |
| 2006/0199790 A1 | 9/2006 | Baulieu et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |
| 2010/0034781 A1 | 2/2010 | Parhami et al. |
| 2010/0087411 A1 | 4/2010 | Barraclough et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1 | 6/2015 | Upasani |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Botella et al. |
| 2017/0247405 A1 | 8/2017 | Harrison et al. |
| 2017/0304321 A1 | 10/2017 | Quirk et al. |
| 2017/0305960 A1 | 10/2017 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0237470 A1 | 8/2018 | Botella et al. |
| 2018/0362573 A1 | 12/2018 | Upasani et al. |
| 2018/0371009 A1 | 12/2018 | Pellicciari et al. |
| 2019/0125764 A1 | 5/2019 | Salituro et al. |
| 2019/0127414 A1 | 5/2019 | Botella et al. |
| 2019/0135854 A1 | 5/2019 | Harrison et al. |
| 2019/0160078 A1 | 5/2019 | Masuoka et al. |
| 2019/0233465 A1 | 8/2019 | Robichaud et al. |
| 2019/0248829 A1 | 8/2019 | Salituro et al. |
| 2019/0330259 A1 | 10/2019 | Robichaud et al. |
| 2019/0359646 A1 | 11/2019 | Botella et al. |
| 2020/0002371 A1 | 1/2020 | Salituro et al. |
| 2020/0024300 A1 | 1/2020 | Salituro et al. |
| 2020/0123195 A1 | 4/2020 | Salituro et al. |
| 2021/0040138 A1 | 2/2021 | Harrison et al. |
| 2021/0101925 A1 | 4/2021 | Salituro et al. |
| 2021/0145848 A1 | 5/2021 | Salituro et al. |
| 2021/0147468 A1 | 5/2021 | Salituro et al. |
| 2021/0147470 A1 | 5/2021 | Upasani et al. |
| 2021/0380631 A1 | 12/2021 | Salituro et al. |
| 2022/0024968 A1 | 1/2022 | Salituro et al. |

FOREIGN PATENT DOCUMENTS

| | | |
|---|---|---|
| CN | 1254716 | 5/2008 |
| FR | 2850023 | 7/2004 |
| GB | 1564806 | 4/1980 |
| JP | 50140435 | 11/1975 |
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 08268917 | 10/1996 |
| JP | 09328498 | 12/1997 |
| JP | H11509844 A | 8/1999 |
| JP | 2005508368 | 3/2005 |
| RU | 2194712 | 12/2002 |
| WO | WO1980002562 | 11/1980 |
| WO | WO1994027608 | 12/1994 |
| WO | WO1995002409 | 1/1995 |
| WO | WO1995013287 | 5/1995 |
| WO | WO1995021617 | 8/1995 |
| WO | WO1996012705 | 5/1996 |
| WO | WO1996040043 | 12/1996 |
| WO | WO1997000884 | 1/1997 |
| WO | WO1997003677 | 2/1997 |
| WO | WO1997042215 | 11/1997 |
| WO | WO1998007740 | 2/1998 |
| WO | WO1999058497 | 11/1999 |
| WO | WO2000063228 | 10/2000 |
| WO | WO2000068246 | 11/2000 |
| WO | WO2001049703 | 7/2001 |
| WO | WO2002011708 | 2/2002 |
| WO | WO2002053577 | 7/2002 |
| WO | WO2002079221 | 10/2002 |
| WO | WO2003039480 | 5/2003 |
| WO | WO2003049685 | 6/2003 |
| WO | WO2003082893 | 10/2003 |
| WO | WO2004055201 | 7/2004 |
| WO | WO2005079810 | 9/2005 |
| WO | WO2008041003 | 4/2008 |
| WO | WO2009001097 | 12/2008 |
| WO | WO2009059961 | 5/2009 |
| WO | WO2009073186 | 6/2009 |
| WO | WO2009090063 | 7/2009 |
| WO | WO2010075282 | 7/2010 |
| WO | WO2010088414 | 8/2010 |
| WO | WO2011014661 | 2/2011 |
| WO | WO2011028794 | 3/2011 |
| WO | WO2011067501 | 6/2011 |
| WO | WO2011092127 | 8/2011 |
| WO | WO2012064501 | 5/2012 |
| WO | WO2012142039 | 10/2012 |
| WO | WO2013019711 | 2/2013 |
| WO | WO2013036835 | 3/2013 |
| WO | WO2013056181 | 4/2013 |
| WO | WO2013163455 | 10/2013 |
| WO | WO2014025942 | 2/2014 |
| WO | WO2014028942 | 2/2014 |
| WO | WO2014115167 | 7/2014 |
| WO | WO2014120786 | 8/2014 |
| WO | WO2014160441 | 10/2014 |
| WO | WO2014160480 | 10/2014 |
| WO | WO2015195967 | 12/2015 |
| WO | WO2016007762 | 1/2016 |
| WO | WO2016057713 | 4/2016 |
| WO | WO2017007832 | 1/2017 |
| WO | WO2017007836 | 1/2017 |
| WO | WO2017007840 | 1/2017 |
| WO | WO2017037465 | 3/2017 |
| WO | WO2017173358 | 10/2017 |
| WO | WO2018064649 | 4/2018 |
| WO | WO2018075698 | 4/2018 |
| WO | WO2018075699 | 4/2018 |
| WO | WO2018170336 | 9/2018 |

OTHER PUBLICATIONS

U.S. Appl. No. 16/089,896, filed Sep. 28, 2018, Albert Jean Robichaud et al., Pending.

U.S. Appl. No. 16/227,013, filed Dec. 20, 2018, Gabriel Martinez Botella et al., Pending.

U.S. Appl. No. 16/338,315, filed Mar. 29, 2019, Francesco G. Salituro et al., Pending.

U.S. Appl. No. 16/343,235, filed Apr. 18, 2019, Francesco G. Salituro et al., Pending.

U.S. Appl. No. 16/343,238, filed Apr. 18, 2019, Francesco G. Salituro et al., Pending.

U.S. Appl. No. 16/943,649, filed Jul. 30, 2020, Francesco G. Salituro et al., Pending.

Bjorkhem et al., "Oxysterols in the circulation of patients with the Smith-Lemli-Opitz syndrome: abnormal levels of 24S- and 27-hydroxycholesterol," Journal of Lipid Research, 4230:366-371 (2001).

Bukelis et al., "Smith-Lemli-Opitz syndrome and autism spectrum disorder," American Journal of Psychiatry, 164:1655-1661 (2007).

Cancer [online], [retrieved on Jul. 6, 2007]. Retrieved from the internet, URL http://www.nlm.nih.gov/medlineplus/ cancer.html> (11 pages).

(56) References Cited

OTHER PUBLICATIONS

Chen et al., "The chemical biology of clinical tolerated NMDA receptor antagonists," Journal of Neurochemistry, 97(6):1611-1626 (2006).
Citraro et al., "Effects of some neurosteroids injected into some brain areas of WAG/Rij rats, an animal model of generalized absence epilepsy," Neuropharmacology, 50(8):1059-1071 (2006).
Collingridge et al., "The NMDA receptor as a target for cognitive enhancement," Neuropharmacology, 64:13-26 (2013).
Connick et al., "Program No. 613 1/B86," 2009 Neuroscience Meeting Planner, Chicago, IL: Society for Neuroscience (2009) (2 pages).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).
Corman et al., "Structure-activity relationships for side chain oxysterol agonists of the hedgehog signaling pathway," ACS Medicinal Chemistry Letters, 3:828-833 (2012).
Cross et al., "Steroids CCLXXIN 1. Biologically-active labile ethers IV2. The synthesis of 22-oxa-25-azacholesterol and related compounds," Steroids, Elsevier Science Publishers, 5(5):585-598 (1965).
Dayal et al., "Stereospecific synthesis of 3b-hydroxylated bile alcohols," Journal of Lipid Research, 25(6):646-650 (1984).
Deng et al., "Fluoro analogs of bioactive oxy-steroids: Synthesis of an EBI2 agonist with enhanced metabolic stability," Bioorganic and Medicinal Chemistry Letters, 26:4888-4891 (2016).
Domasio, "Alzheimer's disease and related dementias," Cecil Textbook of Medicine, 20th edition, 2:1992-1996 (1996).
Elbarbry et al., "Cyclosporine-induced changes in drug metabolizing enzymes in hyperlipemic rabbit kidneys could explain its toxicity," Synthetic Communications, 40(11):772-781 (2010).
European Search Partial Supplementary Report for European Application No. 14775126.7, dated Sep. 14, 2016 (7 pages).
Extended European Search Report for Application No. 15809462.3, dated Nov. 29, 2017 (8 pages).
Extended European Search Report for Application No. 16821920.2, dated Jan. 31, 2019 (12 pages).
Extended European Search Report for Application No. 16821924.4, dated Jan. 31, 2019 (12 pages).
Extended European Search Report for Application No. 16821926.9, dated Jan. 31, 2019 (10 pages).
Extended European Search Report for European Application No. 14774060.9, dated Aug. 17, 2016 (11 pages).
Extended European Search Report for European Application No. 14775126.7, dated Dec. 15, 2016 (6 pages).
Extended European Search Report for European Application No. 15849514.3, dated May 23, 2018 (7 pages).
FDA mulls drug to slow late-stage Alzheimer's [online] (cnn.com/health), [retrieved on Sep. 23, 2003]. Retrieved from the Internet, URL;http://www.cnn.com/2003/HEALTH/conditions/09/24/alzheimers.drug.ap/indexhtml> (2 pages).
Festa et al., "Exploitation of cholane scaffold for the discovery of potent and selective farnesoid X receptor (FXR) and G-protein coupled bile acid receptor 1 (GP-BAR1) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Golub et al., "Molecular classification of cancer: class discovery and class prediction by gene expression monitoring," Science, 286:531-537 (1999).
Gunatilaka et al., "Bioactive ergost-5-ene-3b, 7a-diol derivatives from *Pseudobersama mossambicensis*," Journal of Natural Products, 55(11):1648-1654 (1992).
Hoffmeister et al., "Zur chemie des ecdysons, III: Vergleichende spektrometrische untersuchungen an a.b-ungesättigten steroidketonen," Chemische Berichte, 98:2361-2375 (1965).
Iida et al., "An improved method for the capillary gas chromatographic derivatization of polyhydroxylated steroids having tert-hydroxyl groups," Analytical Sciences, 19:1317-1321 (2003).
Karaki et al., "Structure-activity relationship studies of Niemann-Pick type C1-like 1 (NPC1L1) ligands identified by screen assay monitoring pharmacological chaperone effect," Bioorganic and Medicinal Chemistry, 21(17):5297-5309 (2013).
Khripach et al., "Synthesis of (24S)-hydroxy-and (24S)-24,25-epoxycholesterol analogues, potential agonists of nuclear LXR receptors," Russian Journal of Bioorganic Chemistry, 32(6):586-594 (2006).
Knoppert et al., "Position paper: Paediatric age categories to be used in differentiating between listing on a model essential medicines list for children," pp. 1-5 (2007).
Kurosawa et al., "Synthesis of 19-hydroxylated bile acids and identification of 3a,7a,12a,19-tetrahydroxy-5b-cholan-24oic acid in human neonatal urine," Chemical and Pharmaceutical Bulletin, 43(9):1551-1557 (1995).
Lakhan et al., "Frontiers in Psychiatry, NMDA receptor activity in neuropsychiatric disorders," Fronter Psychiatry, 4:1-7 (2013).
Lala et al., "Role of nitric oxide in tumor progression: Lessons from experimental tumors," Cancer and Metastasis Reviews, 17(1):91-106 (1998).
Layzer, "Section five-degenerative diseases of the nervous system," Cecil Textbook of Medicine, 20th edition, 2:2050-2057 (1996).
Leoni et al., "Oxysterols as biomarkers in neurodegenerative diseases," Chemistry and Physics of Lipids, 164:515-524 (2011).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7a-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).
Luu et al., "Oxysterols: Old tale, new twists," Annual Review of Pharmacology and Toxicology, 56:447-467 (2016).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Meljon et al., "Analysis by liquid chromatography-mass spectrometry of sterols and oxysterols in brain of the newborn Dhcr7(Δ3-5/T93M) mouse: a model of Smith-Lemli-Opitz syndrome," Biochemical Pharmacology, 86:43-55 (2013).
Mourino et al., "Studies on vitamin D (calciferol) and its analogs. 15. 24-nor-la,25-dihydroxyvitamin D3 and 24-nor-25¬hydroxy-5,6-trans-vitamin D3," Journal of Medicinal Chemistry, 21(10):1025-1029 (1978).
Nagano et al., "Chemistry and biochemistry of Chinese drugs. Part II. Hydroxylated sterols, cytotoxic towards cancerous cells: synthesis and testing," Journal of Chemical Research, 9:218 (1977).
Olkkonen et al., "Oxysterols and their cellular effectors," Biomolecules, 2(1):76-103 (2012).
Park-Chung et al., "Distinct sites for inverse modulation of N-methyl-D-aspartate receptors by sulfated steroids," Molecular Pharmacology, 52(6):1113-1123 (1997).
Paul et al., "The major brain cholesterol metabolite 24(S)-hydroxycholesterol is a potent allosteric modulator of N-methyl-D-aspartate receptors," The Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).

(56) References Cited

OTHER PUBLICATIONS

PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Jul. 17, 2017 (8 pages).
PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Nov. 12, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).
Pubchem, CID 132021, Ergostan-3,24-diol, Mar. 5, 2018 (15 pages).
Pubchem, CID 54083335, Schembl4961477, Nov. 8, 2016 (13 pages).
Pubchem, CID 54160779, Schembl4961477, Nov. 8, 2016 (13 pages).
Pubchem, CID 58455549, Schembl12198161, Nov. 8, 2016 (13 pages).
Pubchem, CID 65094, 25-Hydroxycholesterol, Nov. 18, 2016 (17 pages).
Pubchem, CID 66966798, Cholane-3alpha,24,-diol, Nov. 8, 2016 (11 pages).
Pubchem, CID 70604305, Schembl11528874, Nov. 8, 2016 (13 pages).
Pubchem, CID 71508953, Mar. 5, 2018 (13 pages).
Reddy, "Pharmacology of endogenous neuroactive steroids," Critical Reviews in Neurobiology, 15(3-4):197-234 (2013).
Registry (STN) [online] CAS Registration No. 1392266-35-1; 13392266-34-0; 1271523-00-2; 185138-08-3; 185138-00-5; 1851387-82-0; 66450-87-1 (2012).
Roh et al., "Neuroprotective effects of ginsenoside Rg3 against 24-Oh-cholesterol-induced cytotoxicity in cortical neurons," Journal of Ginseng Research, 34(3):246-253 (2010).
Schmidt et al., "Inhibitory effect of oxygenated cholestan-3b-ol derivatives on the growth of *Mycobacterium tuberculosis*," Bioorganic & Medicinal Chemistry Letters, 23(22):6111-6113 (2013).
Sepe et al., "Total synthesis and pharmacological characterization of solomonsterol A, a potent marine pregnane-X-receptor agonist endowed with anti-inflammatory activity," Journal of Medicinal Chemistry, 54:4590-4599 (2011).
Stamp et al., "Plasma levels and therapeutic effect of 25-hydroxycholecalciferol in epileptic patients taking anticonvulsant drugs," British Medical Journal, 4(5831):9-12 (1972).

Stastna et al., "Synthesis of C3, C5, and C7 pregnane derivatives and their effect on NMDA receptor responses in cultured rat hippocampal neurons," Steroids, Elsevier Science Publishers, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics, 160C(4): 285-294 (2012).
Takano et al., "Simple synthesis of 3b,24-dihydroxychol-5-en-7-one by oxidative cleavage of the side chain of cholesterol," Chemistry Letters, 14(8):1265-1266 (1995).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694:3452-3455 (2004).
Xiangdong et al., "Highly stereoselective synthesis of 24R,25- and 24S, 25-dihydroxysteroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yan et al., "Characterization of a synthetic steroid 24-keto-cholest-5-en-3b,19-diol as a neuroprotectant," CNS Neuroscience & Therapeutics, 21(6):486-495 (2015).
Yang et al., "New cytotoxic oxygenated sterols from marine bryozoan *Bugula neritina*," Natural Product Research, 25(16):1505-1511 (2011).
Zuliani et al., "Plasma 24S-hydroxycholesterol levels in elderly subjects with late onset Alzheimer's disease or vascular dementia: a case-control study," BMC Neurology, 11(121):1-8 (2011).
Berge et al., "Pharmaceutical salts," Journal of Pharmaceutical Sciences, 66(1):1-19 (1977).
Cais et al., "Temperature dependence of NR1/NR2B NMDA receptor channels," Neuroscience, 151(2):428-438 (2008).
Costa et al., "A novel family of negative and positive allosteric modulators of NMDA receptors," Journal of Pharmacology and Experimental Therapeutics, 335(3):614-21 (2010).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Ferriz et al., "Prodrug Design of Phenolic Drugs", Current Pharmaceutical Designs, vol. 16, pp. 2033-2052 (2010).
Fukuto et al., "Determination of the Mechanism of Demethlenation of (methylenedioxy)phenyl compounds by cytochrome P450 using deuterium isotope effects," Journal of Medicinal Chemistiy, 34(9):2871-2876 (1991).
Gee et al., "GABA-dependent modulation of the Cl- ionophore by steroids in rat brain," European Journal of Pharmacology, 136(3):419-423 (1987).
Groden et al., "Determination of Fura-2 dissociation constants following adjustment of the apparent Ca-EGTA association constant for temperature and ionic strength," Cell Calcium, 12:(4)279-287 (1991).
Grynkeiwicz et at., "A new generation of Ca2+ indicators with greatly improved fluorescence properties," Journal of Biological Chemistry, 260(6):3440-3345 (1985).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistiy, 50(23):4508-4514 (1985).

(56) References Cited

OTHER PUBLICATIONS

Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jurman et al., "Visual identification of individual transfected cells for electrophysiology using antibody-coated beads," Biotechniques, 17(5):876-881 (1994).
Leoni et al., "Changes in human plasma levels of the brain specific oxy sterol 24S-hydroxycholesterol during progression of multiple sclerosis," Neuroscience Letters, 331(3):163-166 (2002).
Lutjohann et al., "Cholesterol homeostasis in human brain: evidence for an age-dependent flux of 24S-hydroxycholesterol from the brain into the circulation," PNAS, 93(18):9799-804 (1996).
Madau et al, Program No. 613.2/B87. 2009 Neuroscience Meeting Planner. Chicago, IL: Society for Neuroscience (2009) (3 pages).
Monyer et al., "Heteromeric NMDA receptors: molecular and functional distinction of subtypes," Science, 256(5060):1217-1221 (1992).
Nagasaka et al., "Oxysterol changes along with cholesterol and vitamin D changes in adult phenylketonuric patients diagnosed by newborn mass-screening," Clinica Chimica Acta, 416:54-59 (2013).
Niemann-Pick overview [online] retrieved from the internet on Jul. 17, 2021 (URL: https://www.mayoclinic.org/diseases-conditions/niemann-pick/symptoms-causes/syc-20355887).
Niemann-Pick diagnosis-treatment [online] retrieved from the internet on Jul. 17, 2021 (URL: https://www.mayoclinic.org/diseases-conditions/niemann-pick/diagnosis-treatment/drc-20355890).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).
Segal, "Pat hippocampal Neurons in Culture: Responses to Electrical and Chemical Stimuli," Journal of Neurophysiology, 50(6):1249-1264 (1983).
Takahashi et al., "Stereochemistry of reduction of the C-24,25 double bond in the conversion of desmosterol into cholesterol," Tetrahedron Letters, 44(2):341-344 (2003).
Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron 33:2725-2736 (1977).
Zhou et al., "Properties of HERG channels stably expressed in HEK 293 cells studied at physiological temperature," Biophysical Journal, 74(1):230-241 (1998).
Papassotiropoulos, et al., "Plasma 24S-hydroxycholesterol a peripheral indicator of neuronal degeneration and potential state marker for Alzheimer's disease", NeuroReport 11(9): 1959-1962 (2000).
Solomon, et al., "Plasma levels of 24S-hydroxycholesterol reflect brain volumes in patients without objective cognitive impairment but not in those with Alzheimer's disease", Neuroscience Letters 462(1): 89-93 (2009).
U.S. Appl. No. 14/343,603, filed Nov. 25, 2014, Ravindra B. Upasani et al., Abandoned.
U.S. Appl. No. 14/775,401, filed Sep. 11, 2015, Kiran Reddy et al., Abandoned.
U.S. Appl. No. 14/775,678, filed Sep. 12, 2015, Gabriel Martinez Botella et al., Abandoned.
U.S. Appl. No. 15/319,504, filed Dec. 16, 2016, Boyd L. Harrison et al., Issued.
U.S. Appl. No. 15/517,886, filed Apr. 7, 2017, Michael C. Quirk et al., Pending.
U.S. Appl. No. 15/588,305, filed May 5, 2017, Gabriel Martinez Botella et al., Abandoned.
U.S. Appl. No. 15/742,422, filed Jan. 5, 2018, Francesco G. Salituro et al., Issued.
U.S. Appl. No. 15/742,424, filed Jan. 5, 2018, Francesco G. Salituro et al., Issued.
U.S. Appl. No. 15/742,425, filed Jan. 5, 2018, Francesco G. Salituro et al., Issued.
U.S. Appl. No. 15/917,263, filed Mar. 9, 2018, Gabriel Martinez Botella et al., Issued.
U.S. Appl. No. 15/917,272, filed Mar. 9, 2018, Gabriel Martinez Botella et al., Abandoned.
U.S. Appl. No. 16/028,790, filed Jul. 6, 2018, Boyd L. Harrison et al., Issued.
U.S. Appl. No. 16/089,896, filed Sep. 28, 2018, Albert Jean Robichaud et al., Abandoned.
U.S. Appl. No. 16/099,122, filed Nov. 5, 2018, Gabriel Martinez Botella et al., Issued.
U.S. Appl. No. 16/114,791, filed Aug. 28, 2018, Ravindra B. Upasani et al., Issued.
U.S. Appl. No. 16/227,013, filed Dec. 20, 2018, Gabriel Martinez Botella et al., Issued.
U.S. Appl. No. 16/227,099, filed Dec. 20, 2018, Francesco G. Salituro et al., Issued.
U.S. Appl. No. 16/315,250, filed Jan. 4, 2019, Francesco G. Salituro et al., Issued.
U.S. Appl. No. 16/338,315, filed Mar. 29, 2019, Francesco G. Salituro et al., Issued.
U.S. Appl. No. 16/343,235, filed Apr. 18, 2019, Francesco G. Salituro et al., Issued.
U.S. Appl. No. 16/343,238, filed Apr. 18, 2019, Francesco G. Salituro et al., Issued.
U.S. Appl. No. 16/879,460, filed May 20, 2020, Francesco G. Salituro et al., Pending.
U.S. Appl. No. 16/902,730, filed Jun. 16, 2020, Boyd L. Harrison et al., Pending.
U.S. Appl. No. 16/938,348, filed Jul. 24, 2020, James J. Doherty, Pending.
U.S. Appl. No. 16/942,235, filed Jul. 29, 2020, Ravindra B. Upasani et al., Pending.
U.S. Appl. No. 16/942,245, filed Jul. 29, 2020, Francesco G. Salituro et al., Pending.
U.S. Appl. No. 16/943,649, filed Jul. 30, 2020, Francesco G. Salituro et al., Allowed.
U.S. Appl. No. 17/242,860, filed Apr. 28, 2021, Albert Jean Robichaud et al., Pending.
U.S. Appl. No. 17/381,829, filed Jul. 21, 2021, Gabriel Martinez Botella et al., Pending.
U.S. Appl. No. 17/386,364, filed Jul. 27, 2021, Francesco G. Salituro et al., Pending.
U.S. Appl. No. 17/395,155, filed Aug. 5, 2021, Francesco G. Salituro et al., Pending.
U.S. Appl. No. 17/396,034, filed Aug. 6, 2021, Francesco G. Salituro et al., Pending.
U.S. Appl. No. 17/476,153, filed Sep. 15, 2021, Francesco G. Salituro et al., Pending.

* cited by examiner

OXYSTEROLS AND METHODS OF USE THEREOF

CROSS-REFERENCE TO RELATED APPLICATION

The present application is a Continuation of U.S. application Ser. No. 16/099,122, filed Nov. 5, 2018, which is a U.S. National Phase Application under 35 U.S.C. § 371 of International Application PCT/US2017/031374, filed May 5, 2017, which claims priority under 35 U.S.C. § 119(e) to U.S. provisional patent application U.S. Ser. No. 62/332,959, filed May 6, 2016. The entire contents of each of the foregoing applications are incorporated herein by reference.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit Ca2+ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are derived from cholesterol and have been shown to potently and selectively modulate NMDA receptor function. New and improved oxysterols are needed that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, N/DA-mediated disorders. These compounds are expected to show improved in vivo potency, pharmacokinetic (PK) properties, oral bioavailability, formulatability, stability, and/or safety as compared to other oxysterols. Further provided are pharmaceutical compositions comprising the compounds of the present invention, and methods of their use and treatment.

In one aspect, provided herein are compounds according to Formula (III):

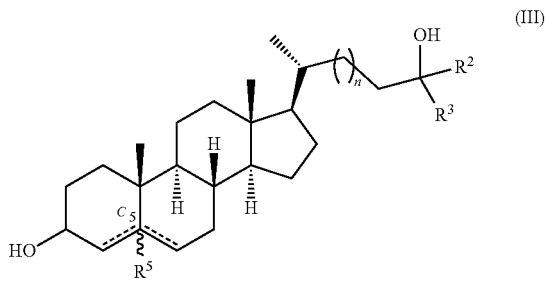

or a pharmaceutically acceptable salt thereof, wherein each of $R^2$ and $R^3$ is independently hydrogen or —$C_{1-6}$ alkyl (e.g., —$C_{1-6}$ haloalkyl); $R^5$ is absent or hydrogen; n is 1 or 2; ==== represents a single or double bond, wherein when one ==== is a double bond, the other ==== is a single bond and $R^5$ is absent; and at least one hydrogen is replaced with a deuterium.

In one aspect, provided herein are compounds according to Formula (II):

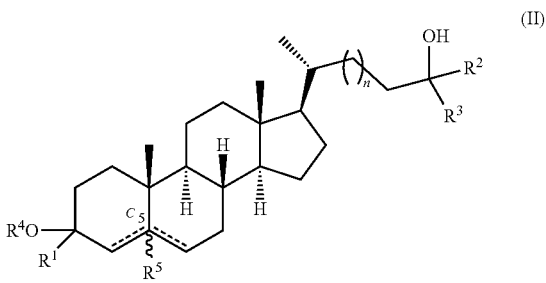

or a pharmaceutically acceptable salt thereof, wherein $R^1$ is hydrogen or deuterium; each of $R^2$ and $R^3$ is independently hydrogen, deuterium or —$C_{1-6}$ alkyl (e.g., —$C_{1-6}$ haloalkyl); $R^4$ is hydrogen or deuterium; $R^5$ is absent, hydrogen, or deuterium; n is 1 or 2; ==== represents a single or double bond, wherein when one ==== is a double bond, the other ==== is a single bond and $R^5$ is absent; and at least one of $R^1$, $R^2$, $R^3$, $R^4$, or $R^5$ is deuterium.

In some embodiments, the compound of Formula (II) is a compound of Formula (I):

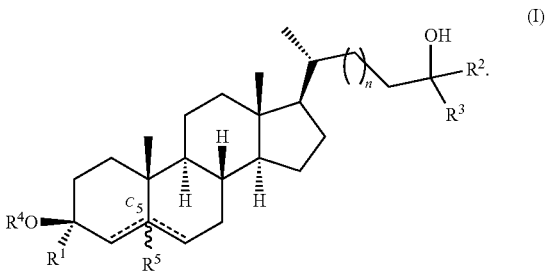

In an aspect, provided herein is a pharmaceutical composition comprising a compound described herein, or pharmaceutically acceptable salt thereof, and a pharmaceutically acceptable carrier.

In an aspect, provided herein is a method of inducing sedation or anesthesia comprising administering to a subject an effective amount of a compound described herein, or pharmaceutically acceptable salt thereof, or pharmaceutical composition thereof.

In an aspect, provided herein is a method for treating or preventing a disorder described herein, comprising administering to a subject in need thereof an effective amount of a compound described herein, or pharmaceutically acceptable salt thereof, or pharmaceutical composition thereof.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis.

In some embodiments, the disorder is inflammatory bowel disease.

In some embodiments, the disorder is cancer, diabetes, or a sterol synthesis disorder.

In an aspect, provided herein is a method for treating or preventing a CNS-related condition comprising administering to a subject in need thereof an effective amount of a compound described herein, or pharmaceutically acceptable salt thereof, or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, or tinnitus.

In some embodiments, the disorder is sterol synthesis disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein (e.g., a compound of Formula (III), (II), or (I)) are deuterium-enriched.

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015% should be considered unnatural and, as a result, novel over their non-enriched counterparts.

The effects of deuterium modification on a compound's metabolic properties are not predictable, even when deuterium atoms are incorporated at known sites of metabolism. Only by actually preparing and testing a deuterated compound can one determine if and how the rate of metabolism will differ from that of its non-deuterated counterpart. See, for example, Fukuto et al. (J. Med. Chem. 1991, 34, 2871-76). Many compounds have multiple sites where metabolism is possible. The site(s) where deuterium substitution is required and the extent of deuteration necessary to see an effect on metabolism, if any, will be different for each compound.

Unless otherwise stated, when a position is designated specifically as "H" or "hydrogen," the position is understood to have hydrogen at its natural abundance isotopic composition. Also unless otherwise stated, when a position is designated specifically as "D" or "deuterium," the position is understood to have deuterium at an abundance that is at least 3000 times greater than the natural abundance of deuterium, which is 0.015% (i.e., the term "D" or "deuterium" indicates at least 45% incorporation of deuterium).

The term "isotopic enrichment factor" as used herein means the ratio between the isotopic abundance of an element at the specified position in a compound of this invention and the naturally occurring abundance of that isotope.

Increasing the amount of deuterium present in a compound (e.g., a compound of Formula (I) is called "deuterium-enrichment," and such compounds are referred to as "deuterium-enriched" compounds. If not specifically noted, the percentage of enrichment refers to the percentage of deuterium present in the compound.

In other embodiments, a compound of this invention has an isotopic enrichment factor for each deuterium present at a site designated at a potential site of deuteration on the compound of at least 3500 (52.5.% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6466.7 (97% deuterium incorporation), at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

Because the natural abundance of deuterium is about 0.015%, approximately one in every 6,667 naturally occurring compounds of Formula (III), e.g., a compound of Formula (I) or (II), would be expected to have one naturally occurring compound of Formula (II), e.g., a compound of Formula (I) or (II), with one deuterium present.

In some embodiments, the compounds of Formula (III) comprise an amount of deuterium-enrichment that is more than the amount of deuterium-enrichment present in naturally occurring compounds of Formula (III).

All percentages given for the amount of deuterium present are mole percentages.

It can be difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

Also described herein is the isolation or purification of deuterium-enriched compounds of Formula (III), e.g., a compound of Formula (I) or (II)). The isolated or purified deuterium-enriched compounds of Formula (III), e.g., a compound of Formula (I) or (II) are above the naturally occurring levels.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 3 substituents, or 1 substituent. In certain embodiments, the alkyl group is unsubstituted $C_{1-4}$ alkyl (e.g., —$CH_3$). In certain embodiments, the alkyl group is substituted $C_{1-4}$ alkyl. Common alkyl abbreviations include Me (—$CH_3$), Et (—$CH_2CH_3$), or iPr (—$CH(CH_3)_2$).

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

These and other exemplary substituents are described in more detail in the Detailed Description, and Claims. The invention is not intended to be limited in any manner by the above exemplary listing of substituents.

Other Definitions

"Halo" or "halogen" refers to fluoro (F), chloro (Cl), bromo (Br), and iodo (I). In certain embodiments, the halo group is either fluoro or chloro.

"Hydroxy" refers to the radical —OH.

Alkyl groups, as defined herein, are optionally substituted (e.g., "substituted" or "unsubstituted" alkyl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$+X$^-$, —N(OR$^C$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R—, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$—P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^a$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ee}$)$_2$, —N(R$^{ee}$)$_2$, —N(R$^{ff}$)$_3$+X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ee}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$), —OP(=O)(R$^{ee}$), —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$alkyl)$_2$+X$^-$, —NH$_2$(C$_{1-6}$ alkyl)+X$^-$, —NH$_3$X$^-$, —N(OC$_{1-6}$ alkyl)(C$_{1-6}$ alkyl), —N(OH)(C$_{1-6}$alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)

($C_{1-6}$ alkyl), —N($C_{1-6}$ alkyl)C(=O)($C_{1-6}$ alkyl), —NHCO$_2$ ($C_{1-6}$ alkyl), —NHC(=O)N($C_{1-6}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$, —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2P_4^-$, $HSO_4^-$, $SO_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$), —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$), —SO$_2$N(R$^{cc}$)$_2$, —SO$_2$R$^{cc}$, —SO$_2$OR$^{cc}$, —SOR$^{aa}$, —C(=S)N(R$^{cc}$), —C(=O)SR$^{cc}$, —C(=S)SR$^{cc}$, —P(=O)$_2$R$^{aa}$, —P(=O)(R$^{aa}$), —P(=O)$_2$N(R$^{cc}$)$_2$, —P(=O)(NR)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Detailed Description of Certain Embodiments of the Invention

As generally described herein, the present invention provides oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols.

Compounds

In one aspect, provided herein are compounds according to Formula (III):

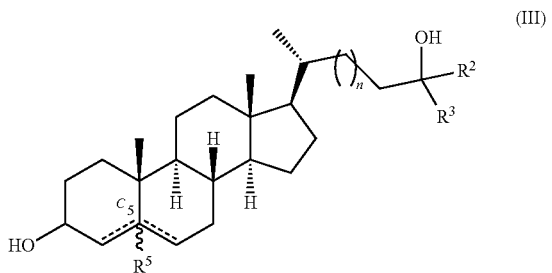

or a pharmaceutically acceptable salt thereof, wherein each of $R^2$ and $R^3$ is independently hydrogen or —$C_{1-6}$ alkyl (e.g., —$C_{1-6}$ haloalkyl); $R^5$ is absent or hydrogen; n is 1 or 2; ==== represents a single or double bond, wherein when one ==== is a double bond, the other ==== is a single bond and $R^5$ is absent; and at least one hydrogen is replaced with a deuterium.

In one aspect, provided herein are compounds according to Formula (II):

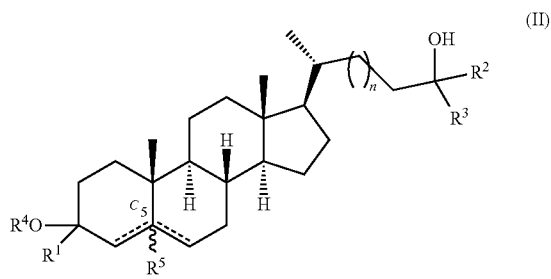

or a pharmaceutically acceptable salt thereof, wherein $R^1$ is hydrogen or deuterium; each of $R^2$ and $R^3$ is independently hydrogen, deuterium or —$C_{1-6}$ alkyl (e.g., —$C_{1-6}$ haloalkyl); $R^4$ is hydrogen or deuterium; $R^5$ is absent, hydrogen, or deuterium; n is 1 or 2; ==== represents a single or double bond, wherein when one ==== is a double bond, the other ==== is a single bond and $R^5$ is absent; and at least one of $R^1$, $R^2$, $R^3$, $R^4$, or $R^5$ is deuterium.

In some embodiments, the compound of Formula (II) is a compound of Formula (I):

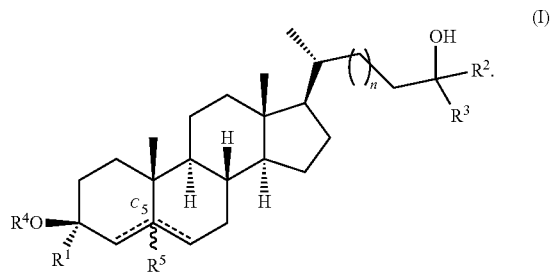

In some embodiments, $R^1$ is hydrogen. In some embodiments, $R^1$ is deuterium.

In some embodiments, one of $R^2$ and $R^3$ is deuterium and the other of $R^2$ and $R^3$ is —$C_{1-6}$ alkyl (e.g., —$C_{1-6}$ haloalkyl). In some embodiments, each of $R^2$ and $R^3$ is independently —$C_{1-6}$ alkyl (e.g., $C_{1-6}$ haloalkyl). In some embodiments, each of $R^2$ and $R^3$ is independently isopropyl, —$CH_3$, or —$CF_3$.

In some embodiments, $R^4$ is hydrogen. In some embodiments, $R^4$ is deuterium.

In some embodiments, ==== represents a single bond. In some embodiments, $R^5$ is hydrogen. In some embodiments, $R^5$ is deuterium.

In some embodiments, ==== represents a double bond and $R^5$ is absent.

In some embodiments, n is 1. In some embodiments, n is 2.

In some embodiments, the compound of Formula (I) is a compound of Formula (I-A):

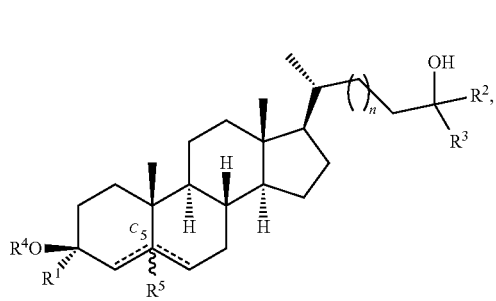

(I-A)

or a pharmaceutically acceptable salt thereof.

In some embodiments, $R^1$ is hydrogen. In some embodiments, $R^1$ is deuterium.

In some embodiments, one of $R^2$ and $R^3$ is deuterium and the other of $R^2$ and $R^3$ is $-C_{1-6}$ alkyl (e.g., $-C_{1-6}$ haloalkyl). In some embodiments, each of $R^2$ and $R^3$ is independently $-C_{1-6}$ alkyl (e.g., $-C_{1-6}$ haloalkyl). In some embodiments, each of $R^2$ and $R^3$ is independently isopropyl, $-CH_3$, or $-CF_3$.

In some embodiments, ═══ represents a single bond. In some embodiments, $R^5$ is hydrogen. In some embodiments, $R^5$ is deuterium.

In some embodiments, ═══ represents a double bond and $R^5$ is absent.

In some embodiments, n is 1. In some embodiments, n is 2.

In some embodiments, the compound of Formula (I) is a compound of Formula (I-B):

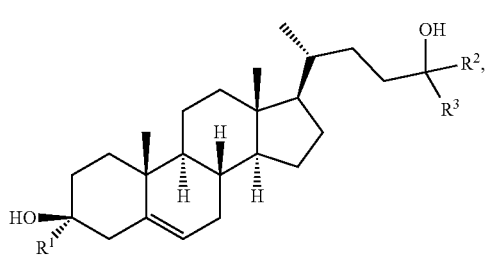

(I-B)

or a pharmaceutically acceptable salt thereof.

In some embodiments, $R^1$ is hydrogen. In some embodiments, $R^1$ is deuterium.

In some embodiments, one of $R^2$ and $R^3$ is deuterium and the other of $R^2$ and $R^3$ is $-C_{1-6}$ alkyl (e.g., $-C_{1-6}$ haloalkyl). In some embodiments, each of $R^2$ and $R^3$ is independently $-C_{1-6}$ alkyl (e.g., $-C_{1-6}$ haloalkyl). In some embodiments, each of $R^2$ and $R^3$ is independently isopropyl, $-CH_3$, or $-CF_3$.

In some embodiments, the compound of Formula (I) is a compound of Formula (I-C):

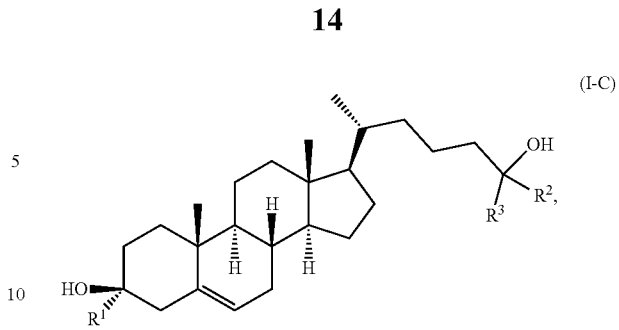

(I-C)

or a pharmaceutically acceptable salt thereof.

In some embodiments, $R^1$ is hydrogen. In some embodiments, $R^1$ is deuterium.

In some embodiments, one of $R^2$ and $R^3$ is deuterium and the other of $R^2$ and $R^3$ is $-C_{1-6}$ alkyl (e.g., $-C_{1-6}$ haloalkyl). In some embodiments, each of $R^2$ and $R^3$ is independently $-C_{1-6}$ alkyl (e.g., $-C_{1-6}$ haloalkyl). In some embodiments, each of $R^2$ and $R^3$ is independently isopropyl, $-CH_3$, or $-CF_3$.

In some embodiments, the compound of Formula (I) is a compound of Formula (I-D):

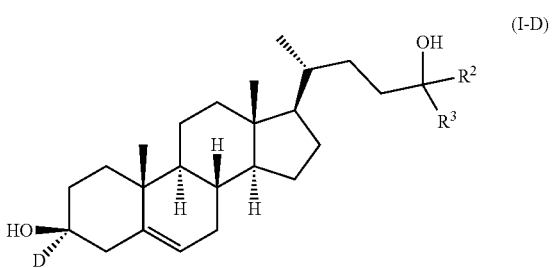

(I-D)

or a pharmaceutically acceptable salt thereof.

In some embodiments, $R^1$ is hydrogen. In some embodiments, $R^1$ is deuterium.

In some embodiments, one of $R^2$ and $R^3$ is deuterium and the other of $R^2$ and $R^3$ is $-C_{1-6}$ alkyl (e.g., $-C_{1-6}$ haloalkyl). In some embodiments, each of $R^2$ and $R^3$ is independently $-C_{1-6}$ alkyl (e.g., $-C_{1-6}$ haloalkyl). In some embodiments, each of $R^2$ and $R^3$ is independently isopropyl, $-CH_3$, or $-CF_3$.

In some embodiments, the compound of Formula (I) is selected from the group consisting of:

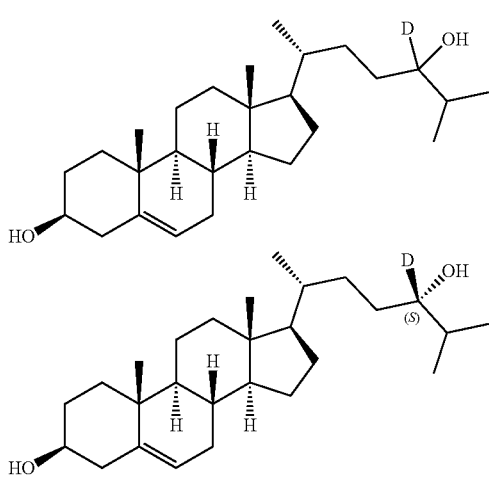

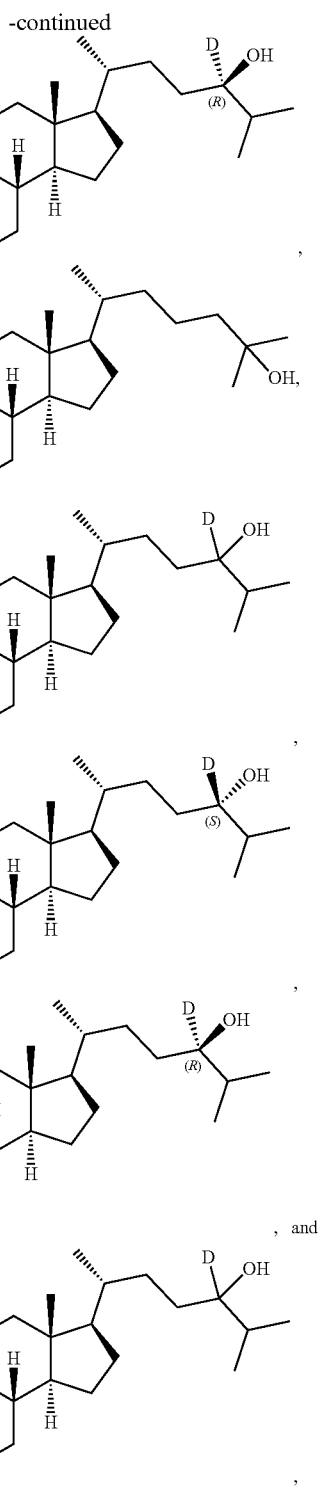

or a pharmaceutically acceptable salt thereof.

Pharmaceutical Compositions

In another aspect, the invention provides a pharmaceutical composition comprising a pharmaceutically acceptable carrier and an effective amount of a compound of Formula (III).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula (III) or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy*, 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences*.

The present invention also relates to the pharmaceutically acceptable formulations of a compound of Formula (III). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of Formula (III). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of Formula (III), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound of Formula (III), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89.50 mg) in water. Sodium benzoate (10 mg), flavor, and color are diluted with water and added with stirring. Sufficient water may then be added to produce a total volume of 5 mL.

Exemplary Formulation 4—Tablets: A compound of Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of Formula (III), or pharmaceutically acceptable salt thereof, may be dissolved or suspended in a buffered sterile saline injectable aqueous medium to a concentration of approximately 5 mg/mL.

Exemplary Formulation 6—Tablets: A compound of Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of Formula (III), or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of Formula (III), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (III), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (III), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound of Formula (III), or pharmaceutically acceptable salt thereof, may act as a negative allosteric modulator (NAM) of NMDA, and inhibit NMDA receptor function. In certain embodiments, the present invention, e.g., a compound of Formula (III), or pharmaceutically acceptable salt thereof, may act as positive allosteric modulators (PAM) of NMDA, and potentiate NMDA receptor function. In creatin embodiments, the compound of Formula (III), or pharmaceutically acceptable salt thereof, modulates NMDA function, but does not act as a negative allosteric modulator (NAM) or positive allosteric modulator (PAM) of NMDA.

In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis. In some embodiments, the disorder is inflammatory bowel disease.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketomuria.

Exemplary conditions related to NMDA-modulation includes, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary CNS conditions related to NMDA-modulation include, but are not limited to, adjustment disorders, anxiety disorders (including obsessive-compulsive disorder, post-traumatic stress disorder, social phobia, generalized anxiety disorder), cognitive disorders (including Alzheimer's disease and other forms of dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, pain (including acute and chronic pain), seizure disorders (including status epilepticus and monogenic forms of epilepsy such as Dravet's disease, and Tuberous Sclerosis Complex (TSC)), stroke, traumatic brain injury, movement disorders (including Huntington's disease and Parkinson's disease) and tinnitus. In certain embodiments, the compound of the present invention, e.g., a compound of Formula (III), or pharmaceutically acceptable salt thereof, can be used to induce sedation or anesthesia. In certain embodiments, the compound of Formula (III), or pharmaceutically acceptable salt thereof, is useful in the treatment or prevention of adjustment disorders, anxiety disorders, cognitive disorders, dissociative disorders, eating disorders, mood disorders, schizophrenia or other psychotic disorders, sleep disorders, substance-related disorders, personality disorders, autism spectrum disorders, neurodevelopmental disorders, sterol synthesis disorders, pain, seizure disorders, stroke, traumatic brain injury, movement disorders and vision impairment, hearing loss, or tinnitus.

In another aspect, provided is a method of treating or preventing brain excitability in a subject susceptible to or afflicted with a condition associated with brain excitability, comprising administering to the subject an effective amount of a compound of the present invention, e.g., a compound of Formula (III), or a pharmaceutically acceptable salt thereof.

In yet another aspect, the present invention provides a combination of a compound of the present invention, e.g., a compound of Formula (III), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Diseases and Disorders

Described herein are methods of treating a sterol synthesis disorder. Exemplary disorders are described herein. The methods include administering to a subject, e.g., a subject suffering from a sterol synthesis disorder such as SLOS, a NMDA receptor modulating compound. Exemplary compounds are described herein.

Sterol Synthesis Disorders

In one aspect, described herein are methods for treating a sterol synthesis disorder. Cholesterol has an essential rule in growth and development. It is a membrane lipid and a precursor to many molecules that play important roles in cellular growth and differentiation, protein glycosylation, and signaling pathways. Biosynthesis of cholesterol involves a number of enzymes and intermediates. Disorders resulting from a deficiency in any of the enzymes involved in cholesterol biosynthesis lead to the accumulation of intermediates and imbalance in biomolecules, resulting in disorders including congenital skeletal malformations, dysmorphic facial features, psychomotor retardation, and failure to thrive. In an embodiment, a sterol synthesis disorder or symptom of a sterol synthesis disorder can be treated by administering to a subject suffering from a sterol synthesis disorder a compound described herein, such as a NMDA receptor modulating compound as described herein. Additional disorders are described below.

Smith-Lemli-Opitz Syndrome

In one aspect, described herein are methods for treating Smith-Lemli-Opitz Syndrome (or SLOS, or 7-dehydrocholesterol reductase deficiency). SLOS is an inborn error of cholesterol synthesis. In addition to microcephaly, moderate to severe intellectual disability, sensory hypersensitivity, stereotyped behaviors, dysmorphic facial features, and syndactyly of the second/third toes, a feature of the disease is reduced cerebrosterol (24(S)-hydroxycholesterol) levels. SLOS is an autosomal recessive genetic condition resulting from deficiency in the final enzyme of the cholesterol synthesis pathway, and causes low or low-normal plasma cholesterol levels and increased 7- and 8-dehydrocholesterol (DHC; 7DHC and 8DHC) levels. Common therapies currently used include dietary cholesterol supplementation, treatment with 3-hydroxy-3-methylglutaryl coenzyme A reductase inhibitors (HMG CoA reductase inhibitors, also known as statins), and treatment with agents that enhance cholesterol production and/or accretion; and to decrease the accumulation of 7DHC and 8DHC, the potentially toxic precursors of cholesterol.

Desmosterolosis

Desmosterolosis is a deficiency in desmosterol reductase and has a similar phenotype to SLOS. In one aspect, described herein are methods for treating desmosterolosis with compounds described herein.

Sitosterolemia

Sitosterolemia is a rare autosomal recessive disorder caused by mutations in two ATP-binding cassette (ABC) transporter genes (ABCG5 and ABCG8). Sitosterolemia enhances the absorption of plant sterols and cholesterol from the intestines. Patients typically present with tendon and tuberous xanthomas and premature coronary artery disease. In one aspect, described herein are methods for treating sitosterolemia with compounds described herein.

Cerebrotendinous Xanthomatosis (CTX)

In one aspect, described herein are methods for treating cerebrotendinous xanthomatosis (also referred to as cerebral cholesterosis, or Van Bogaert-Scherer-Epstein syndrome) with compounds described herein. CTX can be caused by a mutation in the CYP27A1 gene, which produces the sterol 27-hydroxylase enzyme. Sterol 27-hydroxylase metabolizes cholesterol into bile acids (e.g., chenodeoxycholic acid) that are important in the absorption of fats in the intestine. Enzyme dysfunction can lead to cholesterol accumulation in tissues. CTX is characterized by childhood diarrhea, cataracts, tendon xanthomas, reduced mental capability and abnormal movements in adults.

Mevalonate Kinase Deficiency Syndromes (MKD)

Mevalonate Kinase Deficiency (also referred to as mevalonic aciduria (a more severe form of MKD), or Hyper IgD Syndrome (HIDS, or hyperimmunoglobulinemia D) with period fever syndrome (a more benign form of MKD)) causes an accumulation of mevalonic acid in the urine as a result of insufficient activity of mevalonate kinase. MKD can result in developmental delay, hypotonia, anemia, hepatosplenomegaly, dysmorphic features, mental retardation, and overall failure to thrive. Mevalonic aciduria is characterized by delayed physical and mental development, failure to thrive, recurrent episodes of fever with vomiting and diarrhea, enlarged liver, spleen and lymph nodes, microcephaly (small head size), cataract, low muscle tone, short statute, distinct facial features, ataxia, and anemia. HIDS is characterized by recurrent episodes of fever associated with swollen lymph nodes, joint pain, gastrointestinal issues and skin rash. In one aspect, described herein are methods for treating MKD with the compounds described herein.

SC4MOL Gene Mutation (SMO Deficiency)

SC4MOL gene deficiency is a genetic disorder in the cholesterol biosynthesis pathway (e.g., mutations in the SC4MOL gene encoding a novel sterol oxidase). SC4MOL deficiency is characterized by the accumulation of dimethyl and monomethyl sterols that can be detected in blood, skin flakes or primary skin fibroblasts. In one aspect, described herein are methods for treating SMO deficiency with compounds described herein.

Niemann-Pick Disease

Niemann-Pick disease is a lysosomal storage disease resulting from a genetic mutation that affects metabolism. Niemann-Pick disease leads to abnormal accumulation of cholesterol and other fatty substances (lipids) due to an inability of the body to transport the substances. The accumulation damages the affected areas.

Autism

In one aspect, described herein are methods for treating autism spectrum disorder or autism. Autism spectrum disorder (ASD) and autism refer to a group of complex disorders of brain development. Autism is typically characterized by difficulties in social interaction, for example in verbal and nonverbal communication. Repetitive behaviors are also often seen in individuals having autism. Autism can be associated with intellectual disability, difficulties in motor coordination and attention and physical health issues, e.g., sleep and gastrointestinal disturbances. Individuals having autism can also excel in visual skills, music, math and art. Autism can refer to autistic disorder, childhood disintegrative disorder, pervasive developmental disorder-not otherwise specified (PDD-NOS), and Asperger syndrome. Autism also refers to monogenetic causes of autism such as synaptophathy's, e.g., Rett syndrome, Fragile X syndrome, Angelman syndrome.

Disorders Associated with Phenylketonuria

In one aspect, described herein are methods for treating disorders associated with phenylketonuria (e.g., cognitive disorders) with compounds described herein. Phenylketonuria can lead to hypochesterolemia and lowered vitamin D status. Total and low-density cholesterols and 25-hydroxy vitamin D have been found to be decreased in subjects suffering from phenylketonuria as compared with subjects not suffering from phenylketonuria (*Clin. Chim. Acta* 2013, 416: 54-59). 24S-hydroxycholesterol and 27S-hydroxycholesterol and 7α-hydroxycholesterol (e.g., representing peripheral and hepatic cholesterol elimination, respectively) have been shown to be significantly decreased in subjects suffering from phenylketonuria, while 7β-hydroxycholesterol (e.g., reflecting oxidative stress) was increased significantly in subjects suffering from phenylketonuria. Changes in the levels of 24S-OHC and 7β-hydroxycholesterol correlate with phenylalanine level, and 27S-hydroxycholesterol levels may correlate with the 25-hydroxy vitamin D level in subjects suffering from phenylketonuria.

Alternative Embodiments

In an alterative embodiment, compounds described herein may also comprise one or more isotopic substitutions other than the substitution of $^1H$ with deuterium. For example, hydrogen may also be $^3H$ (T or tritium); carbon may be, for example, $^{13}C$ or $^{14}C$; oxygen may be, for example, $^{18}O$; nitrogen may be, for example, $^{15}N$, and the like. In other embodiments, a particular isoptope (e.g., $^3H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least at least 60%, at least 65%, at least 70%, at least 75%, at least 80%, at least 85%, at least 90%, at least 95%, at least 99%, or at least 99.9% of the total isotopic abundance of an element that occupies a specific site of the compound.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Synthesis of Compounds 1, 2, and 3

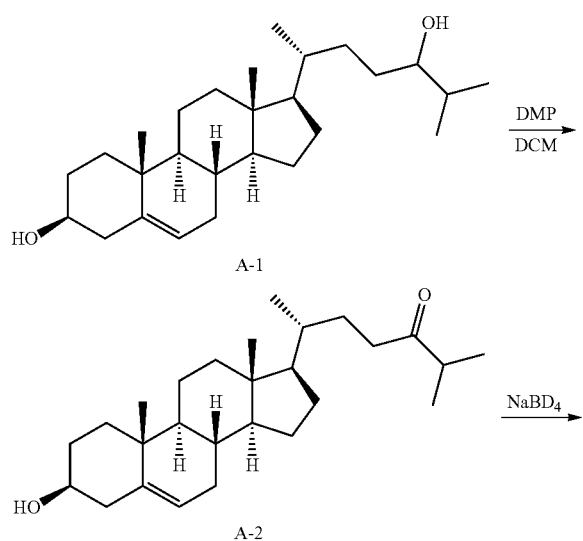

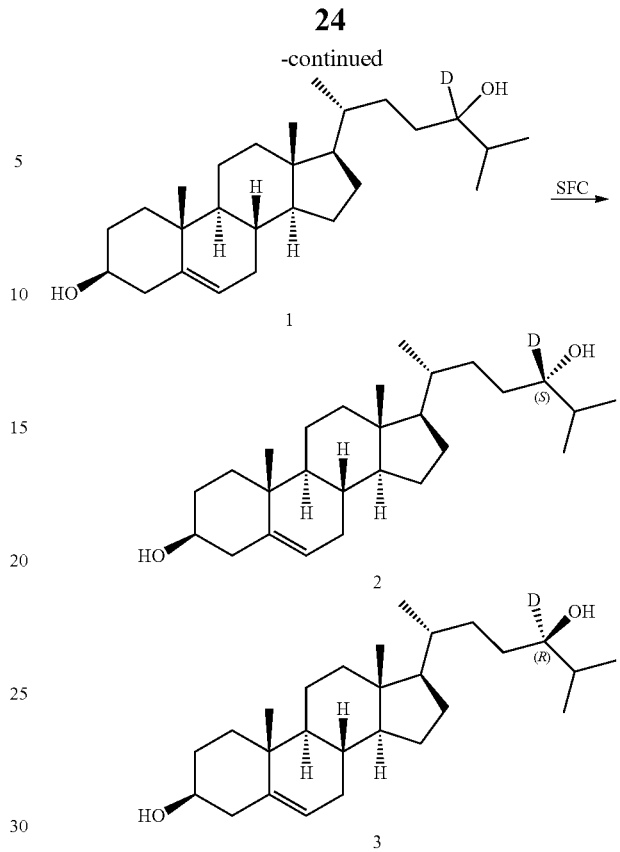

Synthesis of Compound A-2. To a solution of A-1 (1 g, 2.48 mmol) in DCM (50 mL) was added DMP (2.31 g, 5.45 mmol) at 20° C. The mixture was stirred at 20° C. for 30 mins, followed by the addition of water (20 mL) and NaHCO$_3$ (2 g, solid). The mixture was filtered, and the organic phase was separated, washed with saturated Na$_2$S$_2$O$_3$ (50 mL), dried over Na$_2$SO$_4$, filtered, and concentrated under vacuum to give a residue that was purified by column chromatography on silica gel (PE:EtOAc=100:1 to 20:1) to afford A-2 (180 mg, 18%) as an off-white solid. $^1$H NMR (400 MHz, CDCl$_3$) δ 5.40-5.30 (m, 1H), 3.60-3.45 (m, 1H), 2.65-2.15 (m, 5H), 2.05-1.60 (m, 6H), 1.55-1.85 (m, 30H), 0.67 (s, 1H).

Synthesis of Compound 1. To a solution of A-2 (180 mg, 0.45 mmol) in MeOH (15 mL) was added NaBD$_4$ (93.7 mg, 2.24 mmol) at 20° C. The mixture was stirred at 20° C. for 3 mins, then quenched with sat. NH$_4$Cl (20 mL). The solvent was evaporated to ½ volume under vacuum, and the mixture was extracted with DCM (3×20 mL). The combined organic layers were washed with brine (2×50 mL), dried over Na$_2$SO$_4$, filtered, and concentrated under vacuum to give a crude product, which was triturated from PE (10 mL) to give Compound 1 (130 mg, 72%). $^1$H NMR (400 MHz, CDCl$_3$) δ 5.40-5.30 (m, 1H), 3.60-3.45 (m, 1H), 2.35-2.10 (m, 2H), 2.10-1.70 (m, 5H), 1.65-1.59 (m, 3H), 1.55-0.70 (m, 30H), 0.68 (s, 3H). LCMS Rt=1.265 min in 2 min chromatography, MS ESI calcd. for C$_{27}$H$_{44}$DO [M+H-H$_2$O]$^+$ 386, found 386. HRMS MS ESI calcd. for C$_{27}$H$_{45}$DNaO$_2$ [M+Na]$^+$ 426.3453, found 426.3454.

Synthesis of Compounds 2 and 3. Compound 1 (130 mg) was separated by SFC to give Compound 2 (11.5 mg, 11%, D-ratio: 97%) and Compound 3 (19.4 mg, 19%, D-ratio: 98%) as an off-white solid. $^1$H NMR (400 MHz, CDCl$_3$) δ 5.40-5.30 (m, 1H), 3.52 (m, 1H), 2.34-2.18 (m, 2H), 2.05-

1.93 (m, 2H), 1.89-1.78 (m, 3H), 1.72-1.57 (m, 3H), 1.55-0.86 (m, 30H), 0.68 (s, 3H). LCMS Rt=1.210 min in 2 min chromatography, MS ESI calcd. for $C_{27}H_{44}DO$ [M+H-$H_2O$]$^+$ 386, found 386. HRMS MS ESI calcd. for $C_{27}H_{44}DO$ [M+H-$H_2O$]$^+$ 386.3528, found 386.3520.

Example 2. Synthesis of Compound 4

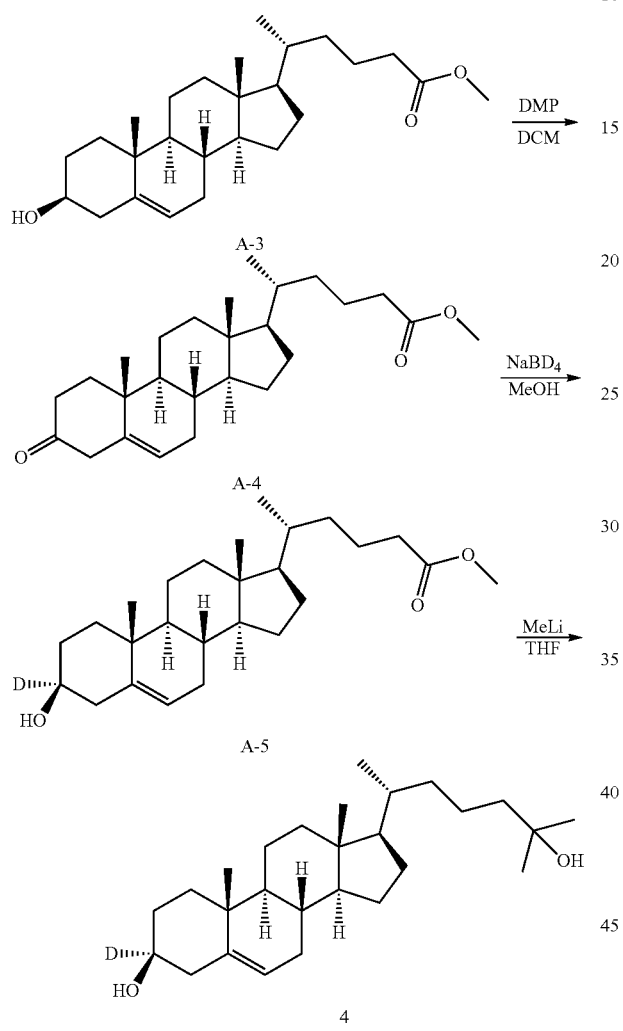

Synthesis of A-4: To a solution of A-3 (1.0 g, 2.48 mmol) in DCM (20 mL) was added DMP (2.10 g, 4.96 mmol) at 0° C. The mixture was stirred at 25° C. for 0.5 h, then quenched with saturated $NaHCO_3/Na_2S_2O_3$=1:3 (15 mL) and extracted with $CH_2Cl_2$ (2×50 mL). The organic phase was washed with brine (50 mL), dried over $Na_2SO_4$, and concentrated. The residue was purified by column chromatography on silica gel (PE/EtOAc=50/1) to afford A-4 (600 mg, 60%) as an off-white solid. $^1$H NMR (400 MHz, $CDCl_3$) δ 5.34-5.29 (m, 1H), 3.66 (s, 3H), 3.29-3.26 (m, 1H), 2.84-2.83 (m, 1H), 2.50-1.57 (m, 10H), 1.54-1.20 (m, 10H), 1.18 (s, 3H), 1.17-0.67 (m, 8H), 0.54 (s, 3H).

Synthesis of A-5: To a solution of A-4 (548 mg, 1.37 mmol) in MeOH (5 mL) was added $NaBD_4$ (69.3 mg, 1.65 mmol) at 20° C. The mixture was stirred at 20° C. for 30 mins, then quenched with saturated $NH_4Cl$ (15 mL) and extracted with EtOAc (2×20 mL). The organic phase was washed with brine (30 mL), dried over $Na_2SO_4$, filtered, and concentrated. The residue was purified by column chromatography on silica gel (PE/EtOAc=15/1) to afford A-5 (290 mg, 52%) as an off-white solid. $^1$H NMR (400 MHz, $CDCl_3$) δ 5.35-5.34 (m, 1H), 3.66 (s, 3H), 2.30-2.23 (m, 4H), 2.05-1.57 (m, 1 OH), 1.53-0.92 (m, 20H), 0.67 (s, 3H).

Synthesis of Compound 4: To a solution of A-5 (250 mg, 619 μmol) in THF (3 mL) was added MeLi (1.93 mL, 3.09 mmol) at 0° C. under $N_2$. The mixture was stirred at 20° C. for 12 hrs, then quenched with saturated $NH_4Cl$ (5 mL) at 0° C. The mixture was treated with water (30 mL) and extracted with EtOAc (2×20 mL). The organic phase was washed with brine (30 mL), dried over $Na_2SO_4$, filtered and concentrated. The residue was purified by column chromatography on silica gel (PE/EtOAc=3/1) to afford Compound 4 (131.8 mg, 53%, deuterated ratio: 97%) as an off-white solid. $^1$H NMR (400 MHz, $CDCl_3$) δ 5.35-5.34 (m, 1H), 2.30-2.27 (m, 2H), 1.99-1.81 (m, 5H), 1.55-1.27 (m, 11H), 1.25-0.92 (m, 23H), 0.64 (s, 3H). LCMS Rt=1.425 min in 2.0 min chromatography, MS ESI calcd. for $C_{27}H_{42}D$ [M+H-$2H_2O$]$^+$ 368, found 368. HRMS MS ESI calcd. for $C_{27}H_{42}D$ [M+H-$2H_2O$]$^+$ 368.3422, found 368.3405.

Example 3. Synthesis of Compounds 5 and 6

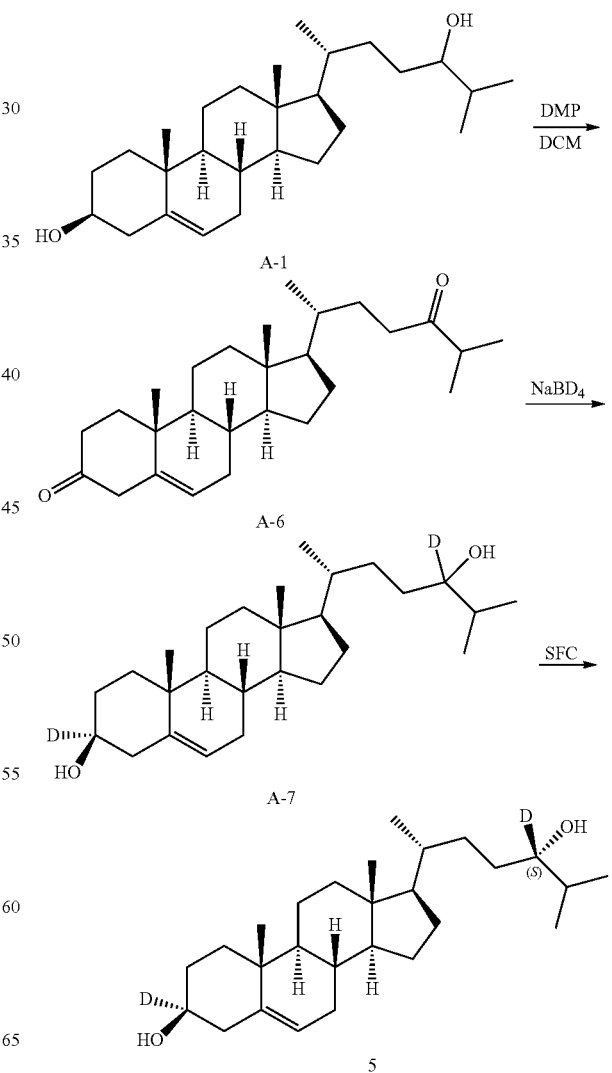

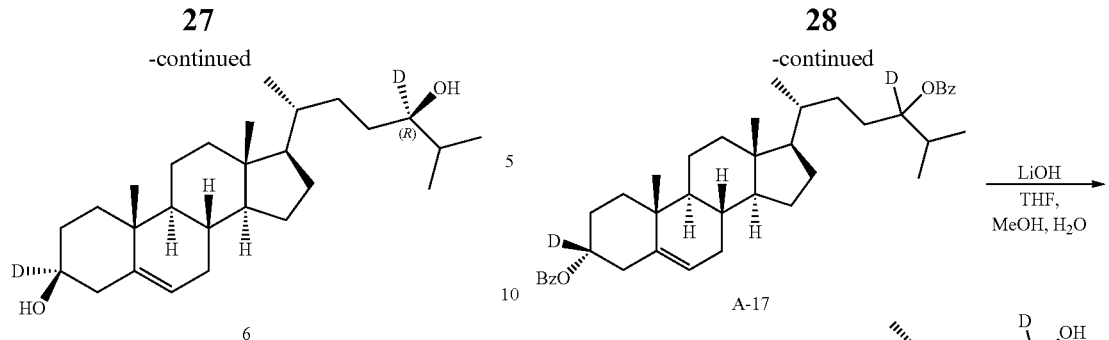

Synthesis of A-6: To a solution of A-1 (500 mg, 1.24 mmol) in DCM (20 mL) was added DMP (5.21 g, 12.3 mmol) at 20° C. The mixture was stirred at 20° C. for 30 mins, then water (10 mL) was added, followed by the addition of NaHCO$_3$ (10 g). The mixture was filtered, and the organic phase was separated, washed with saturated Na$_2$S$_2$O$_3$ (100 mL), dried over Na$_2$SO$_4$, filtered, concentrated under vacuum and purified by column chromatography on silica gel (PE:EtOAc=100:1 to 50:1) to give A-6 (230 mg, 46%) as an off-white solid. $^1$H NMR (400 MHz, CDCl$_3$) δ 5.40-5.30 (m, 1H), 3.35-3.20 (m, 1H), 2.90-2.75 (m, 1H), 2.65-2.20 (m, 6H), 2.10-1.60 (m, 5H), 1.55-0.90 (m, 25H), 0.71 (s, 3H).

Synthesis of A-7: To a solution of A-6 (230 mg) in MeOH (10 mL) was added NaBD$_4$ (2.88 mg, 120 mmol) at 20° C. The mixture was stirred at 20° C. for 2 mins, at which point sat. NH$_4$Cl (20 mL) was added. The mixture was concentrated in vacuum to ½ volume, then extracted with EtOAc (2×30 mL), washed with brine (2×50 mL), dried over Na$_2$SO$_4$, filtered, concentrated under vacuum to give a crude product, which was purified by column chromatography on silica gel (PE:EA=100:1 to 20:1) to give A-7 (170 mg 42%) as an off-white solid. 1H NMR (400 MHz, CDCl$_3$) δ 5.40-5.30 (m, 1H), 2.35-2.10 (m, 2H), 2.10-1.70 (m, 6H), 1.65-1.59 (m, 2H), 1.55-0.70 (m, 30H), 0.68 (s, 3H).

Synthesis of Compounds 5 and 6: A-7 (170 mg) was separated by SFC to give Compound 5 (34 mg, 21%, D-ratio: 99%) as an off-white solid and Compound 6 (45.8 mg, 28%, D-ratio: 99.9%) as an off-white solids. Compound 5: $^1$H NMR (400 MHz, CDCl$_3$) δ 5.40-5.30 (m, 1H), 2.33-2.19 (m, 2H), 2.05-1.93 (m, 2H), 1.90-1.78 (m, 3H), 1.71-1.60 (m, 2H), 1.55-0.85 (m, 31H), 0.68 (s, 3H). LCMS Rt=1.196 min in 2 min chromatography, MS ESI calcd. for C$_{27}$H$_{43}$D$_2$O [M+H-H$_2$O]$^+$ 387, found 387. HRMS MS ESI calcd. for C$_{27}$H$_{44}$D$_2$NaO$_2$ [M+Na]$^+$ 427.3516, found 427.3510. Compound 6: $^1$H NMR (400 MHz, CDCl$_3$) δ 5.40-5.30 (m, 1H), 2.32-2.19 (m, 2H), 2.05-1.92 (m, 2H), 1.91-1.78 (m, 3H), 1.70-1.59 (m, 2H), 1.55-1.40 (m, 8H), 1.37-0.89 (m, 23H), 0.68 (s, 3H). LCMS Rt=1.221 min in 2 min chromatography, MS ESI calcd. for C$_{27}$H$_{43}$D$_2$O [M+H-H$_2$O]$^+$ 387, found 387. HRMS MS ESI calcd. for C$_{27}$H$_{44}$D$_2$NaO$_2$ [M+Na]$^+$ 427.3516, found 427.3511.

Example 4. Synthesis of Compound 7

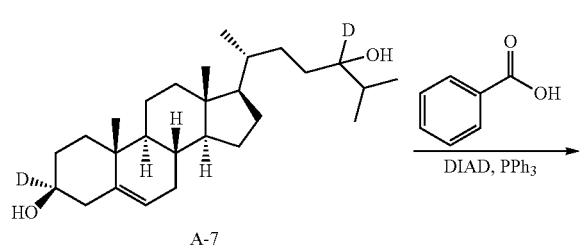

Synthesis of A-17: To a solution of A-7 (330 mg, 0.8 mmol) in THF (20 mL) was added benzoic acid (398 mg, 3.26 mmol) and PPh$_3$ (1.28 g, 4.89 mmol) at 20° C. under N$_2$. The mixture was stirred at 20° C. for 20 mins, at which point DIAD (988 mg, 4.89 mmol) was added at 0° C. under N$_2$. The mixture was stirred at 0° C. for 20 mins, then warmed to 20° C. and stirred at 20° C. for 17 hrs. The mixture was quenched with water (30 mL). The mixture was extracted with EtOAc (2×40 mL), washed with brine (2×80 mL), dried over Na$_2$SO$_4$, filtered and concentrated in vacuum to give A-17 (300 mg, crude), which was used in the next step without further purification. $^1$H NMR (400 MHz, CDCl$_3$) δ 8.15-7.95 (m, 4H), 7.60-7.50 (m, 2H), 7.50-7.40 (m, 4H), 5.35-5.25 (m, 1H), 2.60-2.50 (m, 1H), 2.40-2.30 (m, 1H), 2.10-0.80 (m, 34H), 0.75-0.50 (m, 5H).

Synthesis of Compound 7: To a solution A-17 (300 mg, 0.5 mmol) in THF (5 mL) was added a solution of LiOH (100 mg, 4.17 mmol) in H$_2$O (2 mL) at 10° C. MeOH (3 mL) was added, and the mixture was stirred at 40° C. for 24 hrs. Water (10 mL) was then added, and the mixture was extracted with EtOAc (3×10 mL), washed with sat. NaHCO$_3$ (2×30 mL), brine (2×30 mL), dried over Na$_2$SO$_4$, filtered and concentrated under vacuum to give the crude product (250 mg) as a yellow oil, which was purified by flash column (0-30% EtOAc in PE, 50 min) to give Compound 7 (70 mg, 25%) as an off-white solid. $^1$H NMR (400 MHz, CDCl$_3$) δ 5.50-5.35 (m, 1H), 2.60-2.50 (m, 1H), 2.10-1.60 (m, 1 OH), 1.50-0.80 (m, 29H), 0.68 (s, 3H). LCMS Rt=1.313 min in 2.0 min chromatography, 30-90 AB_E, purity 100%, MS ESI calcd. for C$_{27}$H$_{43}$D$_2$O [M+H-H$_2$O]$^+$ 387, found 387. HRMS MS ESI calcd. for C$_{27}$H$_{43}$D$_2$O [M+H-H$_2$O]$^+$ 387.3590, found 387.3587.

Materials and Methods

The compounds provided herein can be prepared from readily available starting materials using the following general methods and procedures, for example, as described in WO 2013/036835 and WO 2014/160480. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHRALCEL® OJ and CHIRALCEL® OK.

$^1$H-NMR reported herein (e.g., for intermediates) may be a partial representation of the full NMR spectrum of a compound, e.g., a compound described herein. For example, the reported $^1$H NMR may exclude the region between δ (ppm) of about 1 to about 2.5 ppm.

Exemplary general method for preparative HPLC: Column: Waters RBridge prep 10 μm C18, 19*250 mm. Mobile phase: acetonitrile, water ($NH_4HCO_3$) (30 L water, 24 g $NH_4HCO_3$, 30 mL $NH_3.H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 μm at 45° C.

NMDA Potentiation

NMDA potentiation was assessed using either whole cell patch clamp of mammalian cells which expressed NMDA receptors.

Whole-Cell Patch Clamp of Mammalian Cells (Ionworks Barracuda (IWB))

The whole-cell patch-clamp technique was used to investigate the effects of compounds on GlunN1/GluN2A glutamate receptors expressed in mammalian cells. The results are shown on Table 1.

HEK293 cells were transformed with adenovirus 5 DNA and transfected with cDNA encoding the human GRIN1/GRIN2A genes. Stable transfectants were selected using G418 and Zeocin-resistance genes incorporated into the expression plasmid and selection pressure maintained with G418 and Zeocin in the medium. Cells were cultured in Dulbecco's Modified Eagle Medium/Nutrient Mixture (D-MEM/F-12) supplemented with 10% fetal bovine serum, 100 μg/ml penicillin G sodium, 100 μg/ml streptomycin sulphate, 100 μg/ml Zeocin, 5 μg/ml blasticidin and 500 μg/ml G418.

Test article effects were evaluated in 8-point concentration-response format (4 replicate wells/concentration). All test and control solutions contained 0.3% DMSO and 0.01% Kolliphor® EL (C5135, Sigma). The test article formulations were loaded in a 384-well compound plate using an automated liquid handling system (SciClone ALH3000, Caliper LifeScienses). The measurements were perfumed using Ion Works Barracuda platform following this procedure:

Electrophysiological Procedures:
 a) Intracellular solution (mM): 50 mM CsCl, 90 mM CsF, 2 mM $MgCl_2$, 5 mM EGTA, 10 mM HEPES. Adjust to pH 7.2 with CsOH.
 b) Extracellular solution, HB-PS (composition in mM): NaCl, 137; KCl, 1.0; $CaCl_2$, 5; HEPES, 10; Glucose, 10; pH adjusted to 7.4 with NaOH (refrigerated until use).
 c) Holding potential: −70 mV, potential during agonist/PAM application: −40 mV.

Recording Procedure:
 a) Extracellular buffer will be loaded into the PPC plate wells (11 μL per well). Cell suspension will be pipetted into the wells (9 μL per well) of the PPC planar electrode.
 b) Whole-cell recording configuration will be established via patch perforation with membrane currents recorded by on-board patch clamp amplifiers.
 c) Two recordings (scans) will be performed. First, during pre-application of test article alone (duration of pre-application—5 min) and second, during test articles and agonist ($EC_{20}$ L-glutamate and 30 μM glycine) co-application to detect positive modulatory effects of the test article.

Test Article Administration: The first pre-application will consist of the addition of 20 μL of 2× concentrated test article solution and, second, of 20 μL of 1× concentrated test article and agonist at 10 L/s (2 second total application time).

TABLE 1

| Compound | GluN2A PCA IWB Ephys % potentiation at 3 μM |
|---|---|
| 1 | C |
| 2 | B |
| 3 | C |
| 4 | A |
| 5 | C |
| 6 | D |
| 7 | C |

For Table 1, "A" indicates 10 to 75%, "B" indicates potentiation of >75% to 150%; "C" indicates potentiation of >150% to 225%; and "D" indicates potentiation of >225%.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

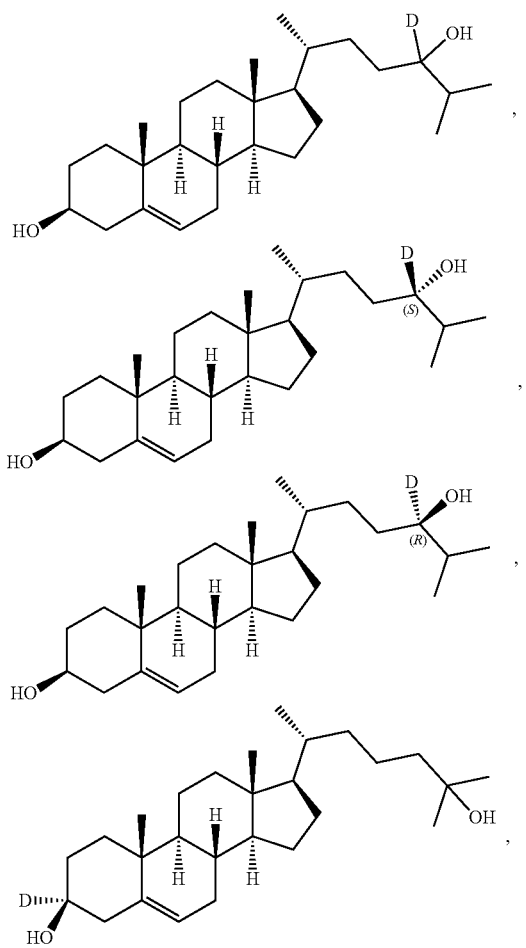

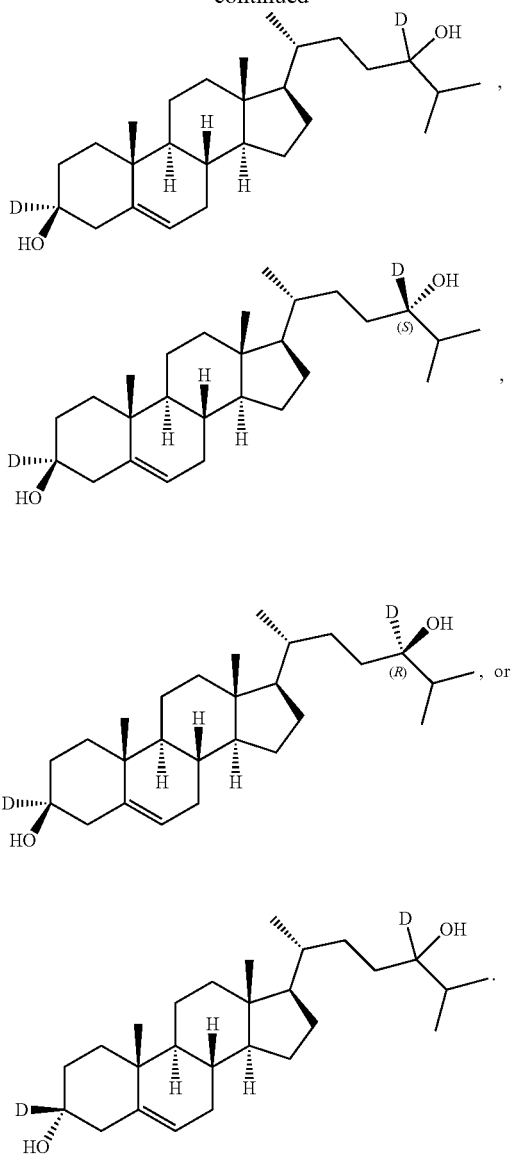

What is claimed is:

1. A pharmaceutical composition comprising a compound of Formula (I):

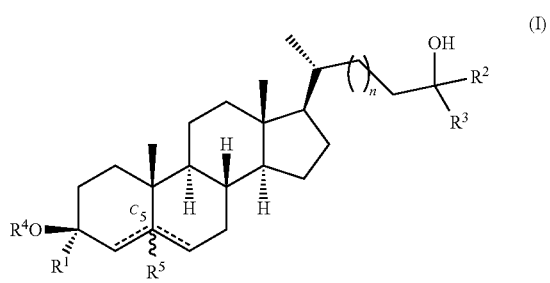

or a pharmaceutically acceptable salt thereof, wherein:
$R^1$ is hydrogen or deuterium;
each of $R^2$ and $R^3$ is independently deuterium or —$C_{1-6}$ alkyl;

$R^4$ is hydrogen or deuterium;
$R^5$ is absent, hydrogen, or deuterium;
n is 1 or 2;
---- represents a single or double bond, wherein when one ---- is a double bond, the other ---- is a single bond and $R^5$ is absent; and
at least one of $R^1$, $R^2$, $R^3$, $R^4$, or $R^5$ is deuterium; and
a pharmaceutically acceptable carrier.

2. The pharmaceutical composition of claim 1, wherein $R^1$ is hydrogen.

3. The pharmaceutical composition of claim 1, wherein $R^1$ is deuterium.

4. The pharmaceutical composition of claim 1, wherein $R^1$ and $R^2$ are deuterium.

5. The pharmaceutical composition of claim 1, wherein one of $R^2$ and $R^3$ is deuterium and the other of $R^2$ and $R^3$ is $C_{1-6}$ alkyl.

6. The pharmaceutical composition of claim 1, wherein each of $R^2$ and $R^3$ is independently —$C_{1-6}$ alkyl.

7. The pharmaceutical composition of claim 1, wherein each of $R^2$ and $R^3$ is independently isopropyl, —$CH_3$, or —$CF_3$.

8. The pharmaceutical composition of claim 1, wherein $R^4$ is hydrogen.

9. The pharmaceutical composition of claim 1, wherein n is 1.

10. The pharmaceutical composition of claim 1, wherein n is 2.

11. The pharmaceutical composition of claim 1, wherein ---- represents a single bond.

12. The pharmaceutical composition of claim 1, wherein the compound of Formula (I) is a compound of Formula (I-A):

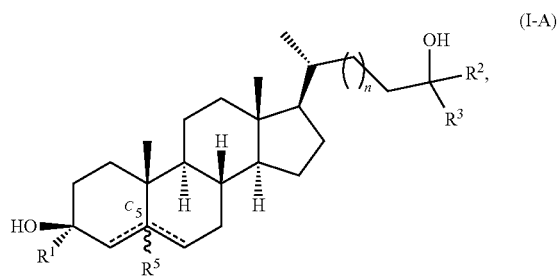

or a pharmaceutically acceptable salt thereof.

13. The pharmaceutical composition of claim 1, wherein the compound of Formula (I) is a compound of Formula (I-B):

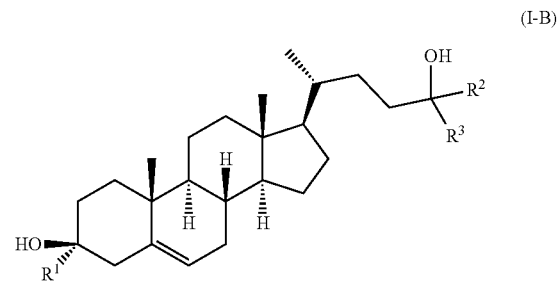

or a pharmaceutically acceptable salt thereof.

14. The pharmaceutical composition of claim 1, wherein the compound of Formula (I) is a compound of Formula (I-C):

(I-C)
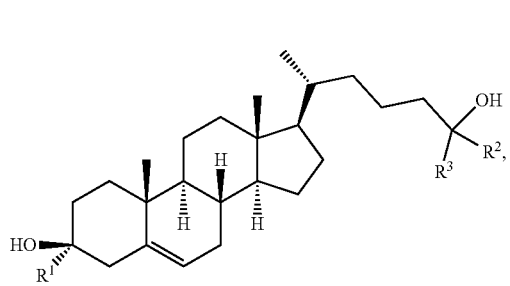

or a pharmaceutically acceptable salt thereof.

15. The pharmaceutical composition of claim 1, wherein the compound of Formula (I) is a compound of Formula (I-D):

(I-D)
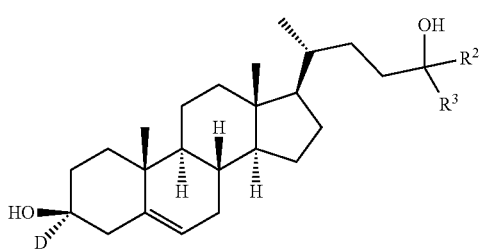

or a pharmaceutically acceptable salt thereof.

16. The pharmaceutical composition of claim 1, wherein the compound of Formula (I) is selected from the group consisting of:

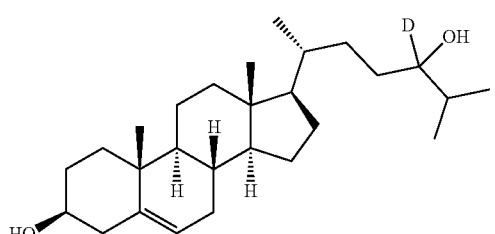,

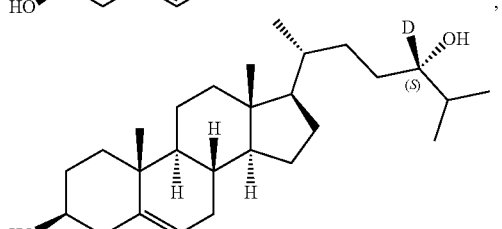,

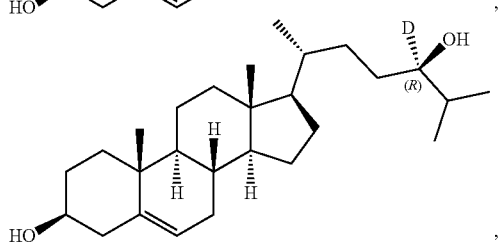,

-continued

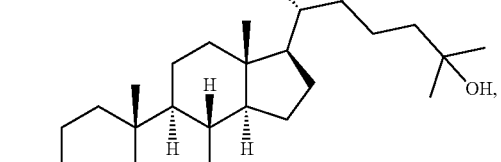,

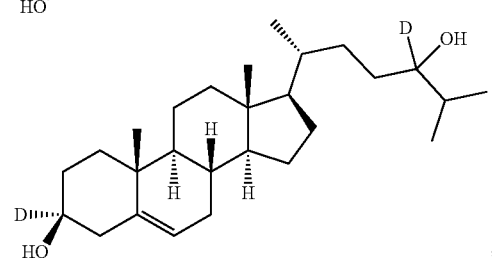,

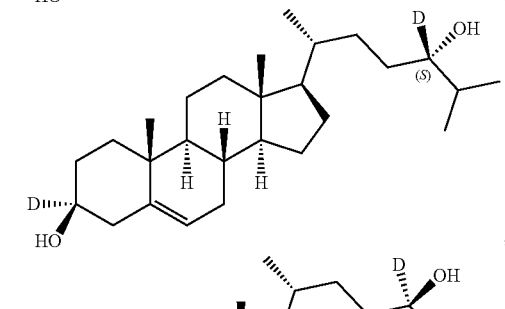, and

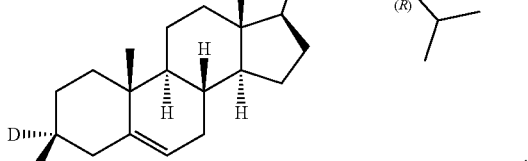.

17. A method of inducing sedation or anesthesia comprising administering to a subject an effective amount of the pharmaceutical composition of claim 1.

18. A method for treating a disorder selected from the group consisting of irritable bowel syndrome (IBS), inflammatory bowel disease (IBD), and colitis, the method comprising administering to a subject in need thereof an effective amount of the pharmaceutical composition of claim 1.

19. The method according to claim 18, wherein the disorder is inflammatory bowel disease.

20. A method for treating a CNS-related condition selected from the group consisting of anxiety disorder, eating disorder, sleep disorder, multiple sclerosis, pain, vision impairment, hearing loss, and tinnitus, the method comprising administering to a subject in need thereof an effective amount of the pharmaceutical composition of claim 1.

21. A method for treating Smith-Lemli-Opitz Syndrome (SLOS), Desmosterolosis, Sitosterolemia, Cerebrotendinous xanthomatosis (CTX), Mevalonate Kinase Deficiency Syndromes (MKD), SC4MOL gene mutation (SMO Deficiency), Niemann-Pick disease, or autism disorders associated with phenylketonuria, comprising administering to a subject in need thereof an effective amount of the pharmaceutical composition of claim 1.

22. The pharmaceutical composition of claim 1, wherein the compound of Formula (I) is a pharmaceutically acceptable salt of